United States Patent [19]

Bachmann et al.

[11] Patent Number: 4,966,172

[45] Date of Patent: Oct. 30, 1990

[54] FLAVOR COMPOSITIONS AND TOBACCO PRODUCTS CONTAINING 3,5,5,6,8,8-HEXAMETHYL-1,2,3,4,5,6,7,8-OCTAHYDRO-2-NAPHTHALENONE

[75] Inventors: Jean-Pierre Bachmann, Bäch; Mario Pesaro, Zurich, both of Switzerland

[73] Assignee: Givaudan Corporation, Clifton, N.J.

[21] Appl. No.: 839,753

[22] Filed: Mar. 14, 1986

[30] Foreign Application Priority Data

Mar. 25, 1985 [CH] Switzerland ............ 1304/85

[51] Int. Cl.$^5$ .............................................. A24B 3/12
[52] U.S. Cl. ................................ 131/276; 426/534
[58] Field of Search ............. 131/276, 277; 424/656, 424/652, 653, 534, 530

[56] References Cited

U.S. PATENT DOCUMENTS 3,773,836 11/1973 Hall .
3,816,350 6/1974 Hall .

FOREIGN PATENT DOCUMENTS 0115274 8/1984 European Pat. Off. .

OTHER PUBLICATIONS

S. Arctander, "Perfume and Flavor Chemicals", I, Steffen Arctander, Montclair, N.J., 1969, Nos. 811, 1581.
H. Brown, "Hydroboration", W. A. Benjamin Inc., New York, 1962, pp. vii–xiii.
D. G. Lee, "Oxidation", 1, R. L. Augustine, editor, Marcel Dekker, Inc., New York, 1969, pp. 56–81.
R. G. Curtis et al., J. Chem. Soc., (1953), 457.

*Primary Examiner*—V. Millin
*Attorney, Agent, or Firm*—Robert F. Tavares; Linda A. Vag

[57] ABSTRACT

Flavor compositions and tobacco products containing 3,5,5,6,8,8-hexamethyl-1,2,3,4,5,6,7,8-octahydro-2-naphthalenone and methods for making same are disclosed.

4 Claims, No Drawings

FLAVOR COMPOSITIONS AND TOBACCO PRODUCTS CONTAINING 3,5,5,6,8,8-HEXAMETHYL-1,2,3,4,5,6,7,8-OCTAHYDRO-2-NAPHTHALENONE

The present invention concerns the novel ketone 3,5,5,6,8,8-hexamethyl-1,2,3,4,5,6,7,8-octahydro-2-naphthalenone, I, a process for the manufacture of I, and fragrance and flavor compositions containing I.

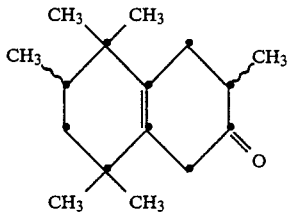
I

Ketone I can exist as a mixture of two possible racemates, Ia and Ib.

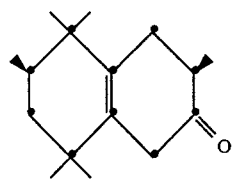
Ia

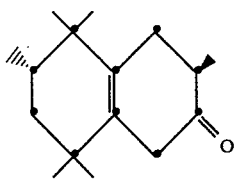
Ib

Formula I is intended to embrace all possible isomers and mixtures thereof.

DESCRIPTION OF THE PREFERRED EMBODIMENTS

Ketone I is prepared by a novel process which comprises the preparation of an organoborane by hydroboration of the bicyclic hydrocarbon 1,1,3,4,4,6-hexamethyl-1,2,3,4,5,8-hexahydronaphthalene, II, followed by oxidation of the organoborane.

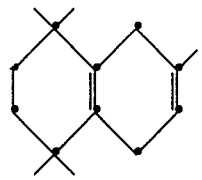
II

In the hydroboration step borane adds across the 6,7-double bond of II. The resulting organoborane can either be oxidized directly to I or can be converted to the alcohol III, which is then oxidized to I.

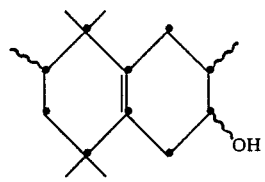
III

Table I below gives a detailed synopsis of the manufacture of I in accordance with the two process variants described above as well as a method for the preparation of hydrocarbon II.

TABLE 1

| Process step | Type of reaction | Reagent | Solvent | Temperature |
|---|---|---|---|---|
| II→organoborane | Hydroboration (1) | $B_2H_6$ | Ether, e.g. diethyl ether, tetrahydrofuran, diglyme, etc. | |
| Organoborane→I | Oxidation | $Cr_2O_7^{2-}/H^+$ ($H_2SO_4$) | | −20−+30° C. esp. room temperature |
| Organoborane→III | Oxidation | $H_2O_2/OH^-$ (NaOH) | | 0−50° C., esp. 0−25° C. |
| III→I | Oxidation alcohol→ketone (2) | Esp. $Cr^{6+}$ salts e.g. Jones' reagent (4) | Acetone | 0−50° C., esp. 0−25° C. |
| Preparation of II | Reduction (3) | (3) | (3) | (3) |

(1) see e.g. Brown, Hydroboration, W. A. Benjamin Inc. N.Y. 1962; borane solutions in tetrahydrofuran are commercially available, but they can also be prepared readily, e.g. by reacting sodium borohydride with boron trifluoride etherate.
(2) see e.g. "Oxidation", Vol. 1, Marcel Bekker Inc. N.Y." (1969) edited by R. L. Augustine, pages 56–81.
(3) reduction of 1,1,3,4,4,6-hexamethyl-1,2,3,4-tetra-hydronaphthalene, see e.g. European Patent Publication No. 115 274 of 8th August 1984.
(4) prepared by dissolving chromium trioxide in concentrated sulphuric acid and diluting with water: J. Chem. Soc., 457(1953).

Ketone I is distinguished by powerful, diffusive and very natural-warm notes in the direction of musk, with fruity, sandalwood-like and animalic aspects. On the basis of its natural olfactory notes I is particularly suitable for modifying fragrance and flavor compositions. A particularly surprising and unexpected aspect of this compound is its extraordinary olfactory strength. The olfactory threshold value is 0.13 ng/l and the olfactory value is 179,800. In contrast, the known and structurally similar 6,7-dihydro-1,1,2,3,3-pentamethyl-5-(4H)-indanone has an olfactory threshold value of 2.5 ng/l and an olfactory value of 35,500, i.e., the odor strength of this compound is much weaker than I. (For a definition of olfactory threshold value and olfactory value see Ulrich A. Huber, Soaps-Oil-Fats-Waxes, 110, No. 15 (1984) 448-451.)

Ketone I combines with numerous known odorant substance ingredients of natural or synthetic origin, whereby the range of the natural raw substances can embrace not only readily volatile but also semi-volatile and difficultly-volatile components, and that of the synthetics can embrace representatives from practically all classes of substances, as is evident from the following compilation:

Natural products, such as tree moss absolute, basil oil, agrumen oils (such as bergamot oil, mandarin oil etc.), mastix absolute, myrtle oil, palmarosa oil, patchouli oil, petitgrain oil, Paraguay, wormwood oil, alcohols, such as farnesol, geraniol, linalool, nerol, phenylethyl alcohol, rhodinol, cinnamic alcohol, aldehydes, such as citral, Helional TM (IFF), α-hexylcinnamaldehyde, hydroxycitronellal, Lilial ® (p-tert. butyl-α-methyl-dihydrocinnamaldehyde), methylnonylacetaldehyde, ketones, such as allylionone, α-ionone, β-ionone, isoraldein (isomethyl-α-ionone), methylionone, esters, such as allyl phenoxyacetate, benzyl salicylate, cinnamyl propionate, citronellyl acetate, citronellyl ethoxalate (citronellyl.O—CO—CO.OC$_2$H$_5$), decyl acetate, dimethylbenzylcarbinyl acetate, dimethylbenzylcarbinyl butyrate, ethyl acetoacetate, ethyl acetylacetate, hexenyl isobutyrate, linalyl acetate, methyl dihydrojasmonate, styrallyl acetate, vetiveryl acetate, lactones, such as γ-undecalactone, various components often used in perfumery, such as musk ketone, indole, p-menthane-8-thiol-3-one, methyleugenol.

Worthy of note is, further, the manner in which the compound I rounds-off and harmonizes the olfactory notes of known compositions without, however, dominating in an unpleasant manner. Thus, it underlines e.g. in perfume bases with tea and green character the soft and flowery notes, and in rose bases the sought-after character of the heavy and sweet Bulgarian rose is underlined.

In fruit bases the compound I can be used with effect to achieve a velvety-soft, natural-sweet and rounded-off effect.

The compound of formula I (or its mixtures) can be used in wide limits which can extend in compositions, for example, from 0.1 (detergents)–5% (alcoholic solutions). It will be appreciated, however, that these values are not limiting values, as the experienced perfumer can also achieve effects with even lower concentrations or can synthesize novel complexes with even higher amounts. The preferred concentrations range between 0.2 and 2%. The compositions manufactured with I can be used for all kinds of perfumed consumer goods (eau de cologne, eau de toilette, extracts, lotions, creams, shampoos, soaps, salves, powders, toothpastes, mouth washes, deodorants, detergents, tobacco, etc.).

The compound I can accordingly be used in the manufacture of compositions and, as will be evident from the above compilation, a wide range of known odorant substances or odorant substance mixtures can be used. In the manufacture of such compositions the known odorant substances enumerated above can be used according to methods known to the perfumer, such as e.g. from W. A. Poucher, Perfumes, Cosmetics and Soaps 2, 7th Edition, Chapman and Hall, London 1974.

The novel compound of formula I is also excellently suited for use in fruit flavours of the widest variety of kind, but especially for the flavouring of tobacco.

As a flavouring substance the compound I can be used, for example, for the production or improvement, intensification, enhancement or modification of fruit flavours of the widest variety of kind, e.g. blackberry or apricot flavours. As fields of use for these flavours there come into consideration, for example, foodstuffs (yoghurt, confectionery, etc.), semi-luxury consumables (tea, tobacco, etc.) and drinks (lemonade etc.).

The pronounced flavour qualities of the compound I enable it to be used as a flavouring substance in low concentrations. A suitable dosage embraces, for example, the range of 0.01 ppm–100 ppm, preferably the range of 0.01 ppm–20 ppm, in the finished product, i.e. the flavoured foodstuff, semi-luxury consumable or drink.

In the flavouring of, for example, tobacco, the dosage can, however, also lie higher and can embrace a wider range, for example the range of 1 to 1000 ppm, preferably 50–500 ppm.

The compound I can be mixed with the ingredients used for flavouring substance compositions or added to such flavourants in the usual manner. Under the flavourants used in accordance with the invention there are to be understood flavouring substance compositions which can be diluted or dispersed in edible materials in a manner known per se. They contain, for example, about 0.1–5, especially 0.2–3, wt. % of compound I. They can be converted according to methods known per se into the usual forms of use such as solutions, pastes or powders. The products can be spray-dried, vacuum-dried or lyophilized.

The known flavouring substances conveniently used in the manufacture of such flavourants are either already contained in the above compilation or can be concluded readily from the respective literature, see e.g.

E. Ziegler, Die natürlichen und künstlichen Aromen, Dr. Alfred Hüthig Verlag GmbH, Heidelberg, 1982.

H. B. Heath, Flavor Technology: Profiles, Products, Applications, Avi Publishing Company, Inc. Westport, Connecticut, 1978.

G. Fenaroli, Fenaroli's Handbook of Flavor Ingredients, Second Edition, Volume 2, CRC-Press, Inc. Cleveland, Ohio 1975, or J. Merory, Food Flavorings, Composition, Manufacture and Use, Second Edition, Avi Publishing Company, Inc., Westport, Connecticut, 1968.

For the manufacture of the usual forms of use there come into consideration, for example, the following carrier materials, thickening agents, flavour improvers, spices and auxillary ingredients, etc.:

Gum arabic, tragacanth, salts or brewers' yeast, alginates, carrageen or similar absorbents, indoles, maltol, dienals, spice oleoresins, smoke flavours: cloves, diacetal, sodium citrate; monosodium glutamate, disodium inosine-5'-monophosphate (IMP), disodium guanosine-5-phosphate (GMP); or special flavouring substances, water, ethanol, propylene glycol, glycerine.

EXAMPLE 1

A solution of 215.4 g of the product of the reduction of 1,1,3,4,4,6-hexamethyl-1,2,3,4-tetrahydronaphthalene with lithium/ethanol in methylamine (containing 58% of 1,1,3,4,4,6-hexamethyl-1,2,3,4,5,8-hexahydronaphthalene in accordance with analysis by gas chromatography) in 580 ml of tetrahydrofuran is treated with 16.23 g of finely powdered sodium borohydride. A solution of 72.5 ml of boron trifluoride ethyl etherate (about 48% BF$_3$) in 116 ml of tetrahydrofuran is added dropwise within 15 minutes and the mixture is stirred at room temperature for 2 hours. After cooling to +5° C. there are added dropwise within 10 minutes 96 ml of water, thereupon within 10 minutes 193 ml of 5N NaOH and finally within 45 minutes 193 ml of 30 percent hydrogen peroxide.

The reaction mixture is stirred at 45° C. for a further 2.5 hours, then taken up in hexane and washed neutral with water. After drying the organic phase over MgSO$_4$ and concentration on a rotary evaporator there remain behind 234.1 g of a colourless oil, the main products of which are the diastereomeric 3,5,5,6,8,8-hexamethyl-1,2,3,4,5,6,7,8-octahydro-2-naphthalenols III.

This oil (234.1 g) is dissolved in 1.06 l of acetone; 291 ml of Jones' reagent are added dropwise at 0° C. in such a manner that the internal temperature does not exceed +5° C. (about 60 minutes). After a further 15 minutes the reaction mixture is taken up in hexane and washed neutral with water; the aqueous phases are extracted with hexane and the organic phase is dried over MgSO$_4$. After concentration there remain behind 208.8 g of a crude oil which are firstly distilled rapidly over a small Vigreux column:

Fractions

75°-96° C./0.07 mbar: 34.5 g;
98°-108° C./0.07 mbar: 146.9 g;
Residue: 22.7 g.

The fraction with boiling point 98°-108° C./0.07 mbar is finely distilled over a 25 cm Widmer column:

Fractions

| | |
|---|---|
| 71-107° C./0.05 mbar, n$_D^{20}$ 1.4892-1.4971 | 53.6 g; |
| 107-113° C./0.05 mbar, n$_D^{20}$ 1.4971-1.4980 | 74.3 g; |
| 113-109° C./0.05 mbar, n$_D^{20}$ 1.5000 | 5.8 g; |
| Residue | 12.2 g. |

The fractions with boiling point 107° C.-113° C./0.05 mbar (74.3 g) are the olfactorily good quality of 3,5,5,6,8,8-hexamethyl-1,2,3,4,5,6,7,8-octahydro-2-naphthalenone (mixture of 2 racemates).

n$_D^{20}$ = 1.4975

IR (CHCl$_3$): 1705 cm$^{-1}$ $^1$H-NMR (400 MHz, CDCl$_3$: δ(ppm) 0.81(s); 0.865(s); 0.89 (d, J=7 Hz); 0.90 (d, J=7 Hz); 0.94(s); 0.96(s); 0.965(s); 0.97(s); 0.98(s); 1.02(s); 1.08 (d, J=7 Hz); 1.09 (d, J=7 Hz): total 18 H. MS (m/e): 234 (M+), 219, 201, 191, 177, 163, 147, 135, 121, 109. Odour: musk-like, slightly sandalwood-like, fruity, animalic.

EXAMPLE 2

A. Flowery Perfumery Base

| | Parts by weight |
|---|---|
| Synthetic jasmine base | 200 |
| Phenylethyl alcohol | 200 |
| Rose base (synthetic) | 200 |
| Musk ketone | 50 |
| Isoraldein (isomethyl-α-ionone) | 50 |
| C-8-aldehyde 10% in DPG | 10 |

-continued

| | Parts by weight |
|---|---|
| (dipropylene glycol) | |
| C-9-aldehyde 10% in DPG | 10 |
| C-10-aldehyde 10% in DPG | 10 |
| C-11-aldehyde 10% in DPG | 10 |
| C-12-aldehyde (lauric aldehyde) 10% in DPG | 10 |
| Dipropylene glycol | 240 |
| | 990 |

The addition of 10 parts of 3,5,5,6,8,8-hexamethyl-1,2,3,4,5,6,7,8-octahydro-2-naphthalenone intensifies the composition and confers to it, in particular, an elegant musk note which is clearly perceptible not only on the freshly dipped smelling strips, but also after 24 hours.

The compound (I) is accordingly suitable, in particular, for feminine lines and for the perfuming of cosmetic products. On the basis of its extraordinary olfactory strength it can also be used diluted in the above composition, e.g. 5 parts of I are also sufficient.

The addition of 10 parts of 6,7-dihydro-1,1,2,3,3-pentamethyl-5(4H)-indanone (U.S. Pat. Nos. 3,773,836, 3,816,350) or of 10 parts of 1,3,4,6,7,8-hexahydro-4,6,6,7,8,8-hexamethyl-cyclopenta-γ-2-benzopyran to this flowery base alters it only to a small extent, it becomes merely soapy and powdery in the first case and slightly fruity in the second case.

If 10 parts of Thibetolide ® (cyclopentadecanolide) are added to the flowery base, then the flowery aspect thereof is underlined insignificantly, the desired improvement of the composition in the direction of musk is, however, only faintly perceptible and, moreover, is manifested only after several hours.

B. Fruity Perfumery Base

| | Parts by weight |
|---|---|
| Hexenyl isobutyrate | 250 |
| Dimethylbenzylcarbinol acetate | 100 |
| Ethyl acetylacetate | 20 |
| Citronellyl acetate | 20 |
| Citronellyl ethoxalate | 20 |
| Decyl acetate | 10 |
| Farnesol | 30 |
| | 450 |

By the addition of 5 parts of 3,5,5,6,8,8-hexamethyl-1,2,3,4,5,6,7,8-octahydro-2-naphthalenone the above composition becomes strongly rounded-off and "harmonized", the fruity pear character of the base now comes into play especially well; the composition becomes softer and is especially suitable for use in cosmetics.

On the other hand, the addition of 5 parts of 6,7-dihydro-1,1,2,3,3-pentamethyl-5-(4H)-indanone (U.S. Pat. Nos. 3,773,836, 3,816,350) or of 5 parts of 1,3,4,6,7,8-hexahydro-4,6,6,7,8,8-hexamethyl-cyclopenta-γ-2-benzopyran or of 5 parts of Thibetolide ® (cyclopentadecanolide) produces only an extremely small effect in this fruity composition, i.e. the aforementioned addition is hardly perceptible.

We claim:

1. A flavor composition comprising a flavoring effective amount of 3,5,5,6,8,8-hexamethyl-1,2,3,4,5,6,7,8-octahydro-2-naphthalenone and at least one other flavor ingredient.

2. A method for improving the flavor of a flavor composition which comprises adding thereto a flavoring effective amount of 3,5,5,6,8,8-hexamethyl-1,2,3,4,5,6,7,8-octahydro-2-naphthalenone.

3. A tobacco product comprising a flavoring effective amount of 3,5,5,6,8,8-hexamethyl-1,2,3,4,5,6,7,8-octahydro-2-napthalenone.

4. A method for improving a tobacco product which comprises adding thereto a flavoring effective amount of 3,5,5,6,8,8-hexamethyl-1,2,3,4,5,6,7,8-octahydro-2-napthalenone.

* * * * *

UNITED STATES PATENT AND TRADEMARK OFFICE
CERTIFICATE OF CORRECTION

PATENT NO. : 4,966,172

DATED : October 30, 1990

INVENTOR(S) : Jean-Pierre Bachmann et al

It is certified that error appears in the above-identified patent and that said Letters Patent is hereby corrected as shown below:

At column 2, lines 10-18, correct figure II

" 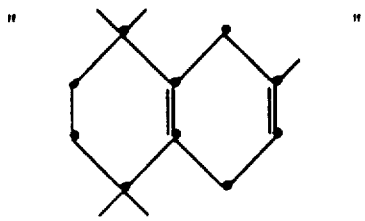 "

to read

-- 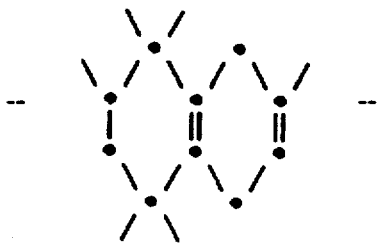 --

Signed and Sealed this

Seventh Day of April, 1992

*Attest:*

HARRY F. MANBECK, JR.

*Attesting Officer*     *Commissioner of Patents and Trademarks*